(12) United States Patent
Goto

(10) Patent No.: US 8,729,302 B2
(45) Date of Patent: May 20, 2014

(54) METHOD OF PRODUCING ACID HALIDE AND ACID HALIDE

(75) Inventor: Akiyoshi Goto, Haibara-gun (JP)

(73) Assignee: FUJIFILM Corporation, Tokyo (JP)

( * ) Notice: Subject to any disclaimer, the term of this patent is extended or adjusted under 35 U.S.C. 154(b) by 194 days.

(21) Appl. No.: 13/194,170

(22) Filed: Jul. 29, 2011

(65) Prior Publication Data

US 2012/0053365 A1    Mar. 1, 2012

(30) Foreign Application Priority Data

Aug. 31, 2010  (JP) ................. 2010-193859

(51) Int. Cl.
*C07C 53/50* (2006.01)

(52) U.S. Cl.
CPC ..................... *C07C 53/50* (2013.01)
USPC ........................................ 562/840

(58) Field of Classification Search
CPC ....................................... C07C 53/50
USPC ........................................ 562/840
See application file for complete search history.

(56) References Cited

U.S. PATENT DOCUMENTS

| 3,367,921 A * | 2/1968 | Sweeny et al. ............... 544/351 |
| 5,155,260 A | 10/1992 | Zubovics et al. |
| 5,235,097 A | 8/1993 | Zubovics et al. |
| 5,312,982 A | 5/1994 | Schubart |
| 6,204,278 B1 | 3/2001 | Shibuya et al. |
| 2005/0107364 A1 | 5/2005 | Hutchinson et al. |

FOREIGN PATENT DOCUMENTS

| EP | 0 068 544 A2 | 1/1983 | |
| EP | 0302312 | * 8/1987 | ............ C07D 239/47 |
| EP | 0466131 | * 1/1992 | ............ C07D 498/04 |
| JP | 04-226936 A | 8/1992 | |
| JP | 05-132446 A | 5/1993 | |

OTHER PUBLICATIONS

Belletire, J.L., Oxidative Coupling of Carboxylic Acid Dianions: The Total Synthesis of rac-Hinokinin and rac-Fometaric Acid, J. Org. Chem. 52, 2549-2555 (1987).*
Zhang et al., Intramolecular [2+2] Cycloaddition and Sequential Ring Expansion, Tetrahedro Letters, 36(16), 2729-2732 (1995).*
Gao, M., et al. Synthesis of Carbon-11 Labeled Triphenyacetamides as Novel Potential PET Melanoma Cancer Imaging Agents, Synthesis, 14, 2301-2304 (2006).*
Hoffman et al., "3-Hydroxy-3-methyloglutaryl-coenzyme A Reductase Inhibitors. 4. Side Chain Derivates of Mevinolin," J. Med. Chem. 29, 849-852, 1986.*
CAS Registry.*
Peter Beak, et al., "Dipole-Stabilized Carbanions: The α Lithiation of Piperridides", J. Am. Chem. Soc., 1984, pp. 1010, No. 4, vol. 106.
Lin Tsai, et al., "Steric Effects in Hydrolysis of Hindered Amides and Nitriles", J. Am. Chem. Soc., May 20, 1957, pp. 2530-2533, vol. 79.
John Anthony MacPhee, et al., "Grignard Reagent-Acid Chloride Condensation in the Presence of Copper (1) Chloride. A Study of Structural Effects by Direct and Competition Methods", Journal of the Chemical Society, Perkin Transactions2: Physical Organic Chemistry, 1974, 1525-30.
Communication, dated Dec. 2, 2011, issued in corresponding EP Application No. 11175931.2, 10 pages.
Curran et al. "On the Mechanism of the Intramolecular Samarium Barbier Reaction. Probes for Formation of Radical and Organosamarium Intermediates," Tetrahedron, vol. 53, No. 27, Jul. 7, 1997, pp. 9023-9042, XP004105846.
Office Action dated Jan. 21, 2014 in Japanese Application No. 2010-193859.

* cited by examiner

*Primary Examiner* — Johann R Richter
*Assistant Examiner* — Mark Luderer
(74) *Attorney, Agent, or Firm* — Sughrue Mion, PLLC

(57) ABSTRACT

A method of producing an acid halide, including: reacting a compound represented by the following Formula (III) with a basic compound and a compound represented by the following Formula (IV) to obtain a compound represented by the following Formula (II); and reacting the compound represented by Formula (II) with an acid halogenating agent to obtain a compound represented by the following Formula (I):

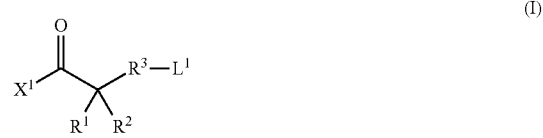

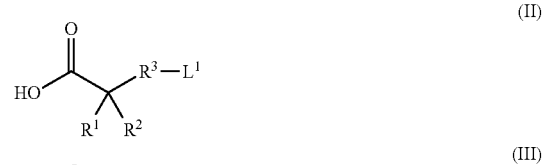

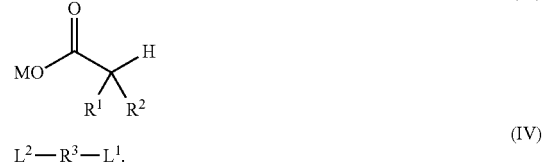

2 Claims, No Drawings

METHOD OF PRODUCING ACID HALIDE AND ACID HALIDE

CROSS-REFERENCE TO RELATED APPLICATION

This application claims priority under 35 USC 119 from Japanese Patent Application No. 2010-193859 filed on Aug. 31, 2010, the disclosure of which is incorporated by reference herein.

BACKGROUND OF THE INVENTION

1. Field of the Invention

The present invention relates to a method of producing an acid halide and the acid halide.

2. Description of the Related Art

The acid halide has been actively used as a synthetic intermediate for functional compounds such as pharmaceutical products and agricultural chemicals, or dyes. Especially, an acid halide having a bulky group enables a particular portion of the functional compound to be bulky. Due to that, it is expected to impart functionalities, for example, realization of a sharp color hue due to prevention of molecular rotation, and enhancement of chemical resistance, weather resistance, or the like due to protection of a fragile portion of the functional compound. Accordingly, the acid halide compound having a bulky group is useful. Further, in an acid halide having both a leaving group and a bulky group, a functional group such as an alkali-soluble group or a polymerizable group can be introduced thereto by replacement of the leaving group, thereby enabling to impart thereto further functionalities. Accordingly, the acid halide compound having both a leaving group and a bulky group is very useful.

As a method of producing an acid halide having a bulky group, there is a method of hydrolyzing an ester compound having a bulky group under alkali conditions, and then bringing the obtained carboxylic acid into reaction with thionyl chloride (for example, refer to J. Am. Chem. Soc. 1984, 106, 1010). However, in the case of producing an acid halide having a leaving group in accordance with the above method, there is a problem that a leaving group is eliminated at the time of producing a carboxylic acid, which results in a yield loss of an objective substance. Especially, the ester compound having a bulky group exhibits such rapid rate of hydrolysis that an elimination reaction progresses conspicuously. Accordingly, it is very difficult to synthesize the acid halide having both a leaving group and a bulky group. In order to suppress elimination of the leaving group, it is considered effective to produce the carboxylic acid having a bulky group under moderate conditions. As for the production methods of carboxylic acid having a bulky group, there are reported a method of reacting acid amide with sodium nitrite (refer to J. Am. Chem. Soc. 1957, 79, 2530), a method of oxidizing a ketone with nitric acid (refer to Journal of the Chemical Society, Perkin Transactions 2: physical Organic Chemistry, 1974, 1525), and a method of reacting a Grignard reagent with carbon dioxide (refer to Journal of the Chemical Society, Perkin Transactions 2: physical Organic Chemistry, 1974, 1525). However, even in these reactions, there are problems that the leaving group also reacts, which results in a yield loss of a target, and further, the reaction is hazardous and resultantly the reaction is not adequate to a mass scale production.

As a synthetic example of the carboxylic acid having a leaving group, a method of hydrolyzing an ester with trimethylsilyl iodide is reported (for example, refer to U.S. Pat. No. 6,204,278). However, there is a problem that trimethylsilyl iodide is expensive and in the case of producing a carboxylic acid having a bulky group, a long time is required for a reaction, which results in high production cost.

Further, in U.S. Pat. No. 6,204,278, synthesis of carboxylic acid chlorides in which a leaving group is a chlorine atom is described. However, any of the described carboxylic acid chlorides has no substituent or has a substituent as small as a methyl group. Accordingly, there is not known a synthetic method of an acid halide having both a leaving group and a bulky group.

SUMMARY OF THE INVENTION

According to an aspect of the invention, there is provided a method of producing an acid halide, comprising:

reacting a compound represented by the following Formula (III) with a basic compound and a compound represented by the following Formula (IV) to obtain a compound represented by the following Formula (II); and reacting the compound represented by Formula (II) with an acid halogenating agent to obtain a compound represented by the following Formula (I):

wherein, in Formula (I), $R^1$ and $R^2$ each independently represent a group selected from the group consisting of an alkyl group, an aryl group, an alkenyl group, an alkynyl group, and a heterocyclic group; $R^3$ represents an alkylene group; $X^1$ represents a halogen atom; and $L^1$ represents a leaving group;

wherein, in Formula (II), $R^1$, $R^2$, $R^3$ and $L^1$ have the same definitions as $R^1$, $R^2$, $R^3$ and $L^1$ in Formula (I), respectively;

wherein, in Formula (III), $R^1$ and $R^2$ have the same definitions as $R^1$ and $R^2$ in Formula (I), respectively, and M represents a hydrogen atom or a metal atom;

wherein, in Formula (IV), $R^3$ and $L^1$ have the same definitions as $R^3$ and $L^1$ in Formula (I), respectively, and $L^2$ represents a leaving group.

DETAILED DESCRIPTION OF THE INVENTION

Hereinafter, a method of producing an acid halide, and the acid halide according to the present invention are described in detail. The description of constituents set forth below may be based on representative exemplary embodiments of the present invention. However, the present invention should not be construed to be limited to theses exemplary embodiments.

In the present invention, the term "bulky group" refers to a group having a steric parameter –Es' value of 1.5 or more.

Note that the term "steric parameter –Es' value" is a parameter that represents a steric bulkiness of a substituent. The –Es' values listed in the literature (J. A. Macphee, et al, Tetrahedron, Vol. 34, pp 3553-3562), and KAGAKU ZOKAN 107 "Kozo kassei Sokan to Doraggu Dezain (Structure Activity Correlation and Drug Design)" compiled and edited by Toshio Fujita, published on Feb. 20, 1986 (KAGAKU-DOJIN PUBLISHING CO., LTD.) are used.

Herein, note that the range of number expressed by using the symbol "-" means to include therein the numbers before and after the symbol "-" as a lower limit and a higher limit respectively.

Regarding notation of a group (atomic group) herein, the notation which does not specify substitution or non-substitution include a group having a substituent in addition to a group having no substituent. For example, the "alkyl group" includes therein not only an alkyl group having no substituent (unsubstituted alkyl group) but also an alkyl group having a substituent (substituted alkyl group). Further, in the case in which a functional group has a substituent, the term "carbon number of the functional group" represents carbon number (s) except for those of the substituent.

The method of producing an acid halide according to the present invention includes: a process of reacting a compound represented by the following Formula (III) with a basic compound and a compound represented by the following Formula (IV), thereby obtaining a compound represented by the following Formula (II); and a process of reacting the compound represented by the following Formula (II) with an acid halogenating agent, thereby obtaining a compound represented by the following Formula (I).

Hereinafter, firstly the compounds represented by the following Formulae (I) to (IV) are described. Next, the method of producing an acid halide according to the present invention is described.

<Compound Represented by Formula (I)>

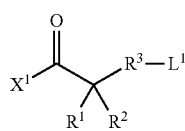

(I)

In Formula (I), $R^1$ and $R^2$ each independently represent a group selected from the group consisting of an alkyl group, an aryl group, an alkenyl group, an alkynyl group, and a heterocyclic group. $R^3$ represents an alkylene group. $X^1$ represents a halogen atom. $L^1$ represents a leaving group.

Each of the alkyl groups represented by $R^1$ and $R^2$ may be a linear or branched alkyl group, or a cyclic alkyl group. Examples of the alkyl group include a linear or branched substituted or unsubstituted alkyl group having 1 to 30 carbon atoms, and a substituted or unsubstituted cycloalkyl group having 3 to 30 carbon atoms.

In a case in which each of $R^1$ and $R^2$ represents a linear or branched alkyl group, the alkyl group is preferably an alkyl group having 1 to 30 carbon atoms, examples of which include a methyl group, an ethyl group, a n-propyl group, an isopropyl group, a t-butyl group, a n-octyl group, a 2-chloroethyl group, a 2-cyanoethyl group, and a 2-ethylhexyl group. Among these groups, a linear or branched substituted or unsubstituted alkyl group having 2 to 20 carbon atoms is preferred. Further, an ethyl group, a propyl group, an isopropyl group, a butyl group, an isobutyl group, a sec-butyl group, and a t-butyl group, all of which are not substituted, are more preferred.

In a case in which each of $R^1$ and $R^2$ represents a cyclic alkyl group, the alkyl group is a substituted or unsubstituted cycloalkyl group. The cycloalkyl group is preferably a cycloalkyl group having 3 to 30 carbon atoms except for carbon atoms of the substituent. Examples of the cycloalkyl group include a cyclopentyl group, a cyclohexyl group, a cycloheptyl group, and a cyclooctyl group.

In a case where an alkyl group has a substituent, examples of the substituent include a halogen atom, an alkyl group, an alkenyl group, an alkynyl group, an aryl group, a heterocyclic group, a cyano group, a hydroxyl group, a nitro group, a carboxyl group, an alkoxy group, an aryloxy group, a silyloxy group, a heterocyclic oxy group, an acyloxy group, a carbamoyloxy group, an amino group (including an alkylamino group and an anilino group), an acylamino group, an aminocarbonylamino group, an alkoxycarbonylamino group, an aryloxycarbonylamino group, a sulfamoylamino group, an alkyl or aryl sulfonylamino group, a mercapto group, an alkylthio group, an arylthio group, a heterocyclic thio group, a sulfamoyl group, a sulfo group, an alkyl or aryl sulfinyl group, an alkyl or aryl sulfonyl group, an acyl group, an aryloxycarbonyl group, an alkoxycarbonyl group, a carbamoyl group, an aryl or heterocyclic azo group, an imido group, a phosphino group, a phosphinyl group, a phosphinyloxy group, a phosphinylamino group, and a silyl group.

The substituent of the alkyl group having a substituent is described below in more detail.

Examples of the substituent include: halogen atoms (for example, fluorine, chlorine, bromine, iodine); alkyl groups (examples include: a linear or branched, substituted or unsubstituted alkyl group having preferably 1 to 30 carbon atoms (for example, methyl, ethyl, n-propyl, isopropyl, t-butyl, n-octyl, 2-chloroethyl, 2-cyanoethyl, and 2-ethylhexyl); and a substituted or unsubstituted cycloalkyl group having preferably 3 to 30 carbon atoms (for example, cyclohexyl, and cyclopentyl), in which the cycloalkyl group may be a polycycloalkyl group, examples of which include: a group having a polycyclic structure such as a tricycloalkyl group and a bicycloalkyl group (preferably a substituted or unsubstituted bicycloalkyl group having 5 to 30 carbon atoms, for example, bicyclo[1,2,2]heptane-2-yl, bicyclo[2,2,2]octane-3-yl). Of these cycloalkyl groups, a monocyclic cycloalkyl group or a bicycloalkyl group is preferred. Especially, a monocyclic cycloalkyl group is preferred.);

an alkenyl group (examples include: a linear or branched, substituted or unsubstituted alkenyl group having preferably 2 to 30 carbon atoms (for example, vinyl, allyl, prenyl, geranyl, oleyl); and a substituted or unsubstituted cycloalkenyl group having preferably 3 to 30 carbon atoms (for example, 2-cyclopentene-1-yl, 2-cyclohexene-1-yl), in which the cycloalkenyl group may be a polycycloalkenyl group, examples of which include: a bicycloalkenyl group (preferably, a substituted or unsubstituted bicycloalkenyl group having 5 to 30 carbon atoms, for example, a bicyclo[2,2,1]hepto-2-ene-1-yl group, a bicyclo[2,2,2]octo-2-ene-4-yl group), and a tricycloalkenyl group. Especially, a monocyclic cycloalkenyl group is preferred.); an alkynyl group (preferably, a substituted or unsubstituted alkynyl group having 2 to 30 carbon atoms, for example, an ethynyl group, a propargyl group, a trimethylsilylethynyl group);

an aryl group (preferably, a substituted or unsubstituted aryl group having 6 to 30 carbon atoms, for example, a phenyl group, a p-tolyl group, a naphthyl group, a m-chlorophenyl group, an o-hexadecanoylaminophenyl group); a heterocyclic group (preferably, a 5- to 7-membered substituted or unsubstituted, saturated or unsaturated, aromatic or non-aromatic, monocyclic or condensed heterocyclic group, more preferably a heterocyclic group having ring-constituting atoms selected from a carbon atom, a nitrogen atom and a sulfur atom, and having at least one hetero atom selected from a nitrogen atom, an oxygen atom and a sulfur atom, and still more preferably a 5- or 6-membered aromatic heterocyclic group having 3 to 30 carbon atoms, for example, a 2-furyl group, 2-thienyl group, a 2-pyridyl group, a 4-pyridyl group, 2-pyrimidinyl group, 2-benzothiazolyl group); a cyano group; a hydroxyl group; a nitro group; a carboxyl group;

an alkoxy group (preferably, a substituted or unsubstituted alkoxy group having 1 to 30 carbon atoms, for example a methoxy group, an ethoxy group, an isopropoxy group, a t-butoxy group, a n-octyloxy group, a 2-methoxyethoxy group); an aryloxy group (preferably, a substituted or unsubstituted aryloxy group having 6 to 30 carbon atoms, for example a phenoxy group, a 2-methylphenoxy group, a 2,4-di-t-aminophenoxy group, a 4-t-butylphenoxy group, a 3-nitrophenoxy group, a 2-tetradecanoylaminophenoxy group); a silyloxy group (preferably, a silyloxy group having 3 to 20 carbon atoms, for example, a trimethylsilyloxy group, a t-butyldimethylsilyloxy group); a heterocyclic oxy group (preferably, a substituted or unsubstituted heterocyclic oxy group having 2 to 30 carbon atoms, in which the heterocyclic moiety is preferably any of those heterocyclic moieties described in the above heterocyclic groups, for example, a 1-phenyltetrazole-5-oxy group, a 2-tetrahydropyranyloxy group);

an acyloxy group (preferably, a formyloxy group, a substituted or unsubstituted alkylcarbonyloxy group having 2 to 30 carbon atoms, a substituted or unsubstituted arylcarbonyloxy group having 6 to 30 carbon atoms, for example, a formyloxy group, an acetyloxy group, a pivaloyloxy group, a stearoyloxy group, a benzoyloxy group, a p-methoxyphenylcarbonyloxy group); a carbamoyloxy group (preferably, a substituted or unsubstituted carbamoyloxy group having 1 to 30 carbon atoms, for example, a N,N-dimethylcarbamoyloxy group, a N,N-diethylcarbamoyloxy group, a morpholinocarbonyloxy group, a N,N-di-n-octylaminocarbonyloxy group, a N-n-octylcarbamoyloxy group); an alkoxycarbonyloxy group (preferably, a substituted or unsubstituted alkoxycarbonyloxy group having 2 to 30 carbon atoms, for example, a methoxycarbonyloxy group, an ethoxycarbonyloxy group, a t-butoxycarbonyloxy group, a n-octyloxycarbonyloxy group); an aryloxycarbonyloxy group (preferably, a substituted or unsubstituted aryloxycarbonyloxy group having 7 to 30 carbon atoms, for example, a phenoxycarbonyloxy group, a p-methoxyphenoxycarbonyloxy group, a p-n-hexadecyloxyphenoxycarbonyloxy group); an amino group (preferably, an amino group, a substituted or unsubstituted alkylamino group having 1 to 30 carbon atoms, a substituted or unsubstituted arylamino group having 6 to 30 carbon atoms, a substituted or unsubstituted heterocyclic amino group having 1 to 30 carbon atoms, for example, an amino group, a methylamino group, a dimethylamino group, an anilino group, an N-methyl-anilino group, a diphenylamino group, an N-1,3,5-triazine-2-yl amino group); an acylamino group (preferably, a formylamino group, a substituted or unsubstituted alkylcarbonylamino group having 1 to 30 carbon atoms, a substituted or unsubstituted arylcarbonylamino group having 6 to 30 carbon atoms, for example, a formylamino group, an acetylamino group, a pivaroylamino group, a lauroylamino group, a benzoylamino group, a 3,4,5-tri-n-octyloxyphenylcarbonylamino group); an aminocarbonylamino group (preferably, a substituted or unsubstituted aminocarbonylamino group having 1 to 30 carbon atoms, for example, a carbamoylamino group, an N,N-dimethylaminocarbonylamino group, an N,N-diethylaminocarbonylamino group, a morpholinocarbonylamino group); an alkoxycarbonylamino group (preferably, a substituted or unsubstituted alkoxycarbonylamino group having 2 to 30 carbon atoms, for example, a methoxycarbonylamino group, an ethoxycarbonylamino group, a t-butoxycarbonylamino group, a n-octadecyloxycarbonylamino group, an N-methyl-methoxycarbonylamino group);

an aryloxycarbonylamino group (preferably, a substituted or unsubstituted aryloxycarbonylamino group having 7 to 30 carbon atoms, for example, a phenoxycarbonylamino group, a p-chlorophenoxycarbonylamino group, a m-n-octyloxyphenoxycarbonylamino group); a sulfamoylamino group (preferably, a substituted or unsubstituted sulfamoylamino group having 0 to 30 carbon atoms, for example, a sulfamoylamino group, an N,N-dimethylaminosulfonylamino group, an N-octylaminosulfonylamino group), an alkyl or aryl sulfonylamino group (preferably, a substituted or unsubstituted alkylsulfonylamino group having 1 to 30 carbon atoms, a substituted or unsubstituted arylsulfonylamino group having 6 to 30 carbon atoms, for example, a methylsulfonylamino group, a butylsulfonylamino group, a phenylsulfonylamino group, a 2,3,5-trichlorophenylsulfonylamino group, a p-methylphenylsulfonylamino group); a mercapto group;

an alkylthio group (preferably, a substituted or unsubstituted alkylthio group having 1 to 30 carbon atoms, for example, a methylthio group, an ethylthio group, an n-hexadecylthio group); an arylthio group (preferably, a substituted or unsubstituted arylthio group having 6 to 30 carbon atoms, for example, a phenylthio group, a p-chlorophenylthio group, an m-methoxyphenylthio group); a heterocyclic thio group (preferably, a substituted or unsubstituted heterocyclic thio group having 2 to 30 carbon atoms, in which the heterocyclic moiety is preferably any of those heterocyclic moieties described in the above heterocyclic groups. For example, a 2-benzothiazolylthio group, a 1-phenyltetrazole-5-yl thio group); a sulfamoyl group (preferably, a substituted or unsubstituted sulfamoyl group having 0 to 30 carbon atoms, for example, an N-ethylsulfamoyl group, an N-(3-dodecyloxypropyl)sulfamoyl group, an N,N-dimethylsulfamoyl group, an N-acetylsulfamoyl group, an N-benzoylsulfamoyl group, an N—(N-phenylcarbamoyl)sulfamoyl group); a sulfo group;

an alkyl or aryl sulfinyl group (preferably, a substituted or unsubstituted alkylsulfinyl group having 1 to 30 carbon atoms, a substituted or unsubstituted arylsulfinyl group having 6 to 30 carbon atoms, for example, a methylsulfinyl group, an ethylsulfinyl group, a phenylsulfinyl group, a p-methylphenylsulfinyl group); an alkyl or aryl sulfonyl group (preferably, a substituted or unsubstituted alkylsulfonyl group having 1 to 30 carbon atoms, a substituted or unsubstituted arylsulfonyl group having 6 to 30 carbon atoms, for example, a methylsulfonyl group, an ethylsulfonyl group, a phenylsulfonyl group, a p-methylphenylsulfonyl group); an acyl group (preferably, formyl group, a substituted or unsubstituted alkylcarbonyl group having 2 to 30 carbon atoms, a substituted or unsubstituted arylcarbonyl group having 7 to 30 carbon atoms, for example, an acetyl group, a pivaloyl group, a 2-chloracetyl group, a stearoyl group, a benzoyl group, a p-n-octyloxyphenylcarbonyl group); an aryloxycarbonyl group (preferably, a substituted or unsubstituted aryloxycarbonyl group having 7 to 30 carbon atoms, for example, a phenoxycarbonyl group, an o-chlorophenoxycarbonyl group, a m-nitro phenoxycarbonyl group, a p-t-butylphenoxycarbonyl group);

an alkoxycarbonyl group (preferably, a substituted or unsubstituted alkoxycarbonyl group having 2 to 30 carbon atoms, for example, a methoxycarbonyl group, an ethoxycarbonyl group, a t-butoxycarbonyl group, a n-octadecyloxycarbonyl group); a carbamoyl group (preferably, a substituted or unsubstituted carbamoyl group having 1 to 30 carbon atoms, for example, a carbamoyl group, an N-methylcarbamoyl group, an N,N-dimethylcarbamoyl group, an N,N-di-n-octyl-carbamoyl group, an N-(methylsulfonyl)carbamoyl group); an aryl or heterocyclic azo group (preferably, a substituted or unsubstituted aryl azo group having 6 to 30 carbon atoms, a substituted or unsubstituted heterocyclic azo group having 3 to 30 carbon atoms (a heterocyclic moiety is preferably any of those heterocyclic moieties described in the above heterocyclic group), for example, a phenylazo group, a p-chlorophenylazo group, a 5-ethylthio-1,3,4-thiadiazole-2-yl azo group); an imido group (preferably, a substituted or unsubstituted imido group having 2 to 30 carbon atoms, for example, an N-succinimido group, an N-phthalimido group); a phosphino group (preferably, a substituted or unsubstituted phosphino group having 2 to 30 carbon atoms, for example, a dimethylphosphino group, a diphenylphosphino group, a methylphenoxyphosphino group); a phosphinyl group (preferably, a substituted or unsubstituted phosphinyl group having 2 to 30 carbon atoms, for example, a phosphinyl group, a dioctyloxyphosphinyl group, a diethoxyphosphinyl group);

a phosphinyloxy group (preferably, a substituted or unsubstituted phosphinyloxy group having 2 to 30 carbon atoms, for example, a diphenoxyphosphinyloxy group, a dioctyloxyphosphinyloxy group); a phosphinylamino group (preferably, a substituted or unsubstituted phosphinylamino group having 2 to 30 carbon atoms, for example, a dimethoxyphosphinylamino group, a dimethylaminophosphinylamino group); and a silyl group (preferably, a substituted or unsubstituted silyl group having 3 to 30 carbon atoms, for example, a trimethylsilyl group, a t-butyldimethylsilyl group, a phenyldimethylsilyl group).

Among the above substituents, the substituent having a hydrogen atom may be further substituted with any of the above substituents by elimination of the hydrogen atom. Examples of such substituent include an alkylcarbonylaminosulfonyl group, an arylcarbonylaminosulfonyl group, an alkylsulfonylaminocarbonyl group, and an arylsulfonylaminocarbonyl group. Specific examples thereof include a methylsulfonylaminocarbonyl group, a p-methylphenylsulfonylaminocarbonyl group, an acetylaminosulfonyl group, and a benzoylaminosulfonyl group.

Each of the alkenyl groups represented by $R^1$ and $R^2$ may be a linear or branched group, or a cyclic group. Examples of the alkenyl group include a substituted or unsubstituted alkenyl group.

In a case in which each of $R^1$ and $R^2$ represents a linear or branched alkenyl group, alkenyl groups having 2 to 30 carbon atoms except for carbon atoms of a substituent are preferred. Specific examples of the alkenyl group include an allyl group, a prenyl group, a geranyl group, and an oleyl group. Examples of the substituent, which the alkenyl group may have, include those listed as examples of the substituent of the above alkyl group.

In a case in which each of $R^1$ and $R^2$ represents a cyclic alkenyl group, the cycloalkenyl groups having 5 to 20 carbon atoms except for carbon atoms of a substituent are preferred. Examples of the cycloalkenyl group include a cyclopentenyl group, a cyclohexenyl group, a cyclooctenyl group, and a cyclodecenyl group. Examples of the substituent, which the cycloalkenyl group may have, include those listed as examples of the substituent of the above alkyl group.

The alkynyl groups represented by $R^1$ and $R^2$ include an alkynyl group having a substituent and an unsubstituted alkynyl group. The alkynyl groups having 2 to 30 carbon atoms except for carbon atoms of the substituent are preferred. Examples of the alkynyl group include an ethynyl group and a propargyl group. Examples of the substituent, which the alkynyl group may have, include those listed as examples of the substituent of the above alkyl group.

The aryl groups represented by $R^1$ and $R^2$ include an aryl group having a substituent and an unsubstituted aryl group. As the aryl groups, those having 6 to 30 carbon atoms except for carbon atoms of the substituent are preferred. Examples of the aryl group include a phenyl group, a p-tolyl group, and a naphthyl group. Examples of the substituent, which the aryl group may have, include those listed as examples of the substituent of the above alkyl group.

The heterocyclic groups represented by $R^1$ and $R^2$ include a heterocyclic group having a substituent and an unsubstituted heterocyclic group. As the heterocyclic groups, those having 6 to 30 carbon atoms except for carbon atoms of the substituent are preferred. Examples of the heterocyclic group include a pyridyl group, an imidazoyl group, a piroyl group, a pyrazolyl group, a furanyl group, and a tetrahydrofuranyl group. Examples of the substituent, which the heterocyclic group may have, include those listed as examples of the substituent of the above alkyl group.

Each of $R^1$ and $R^2$ is preferably an alkyl group in particular.

$R^3$ in Formula (I) represents a substituted or unsubstituted alkylene group which may be linear or branched, or cyclic.

The linear or branched alkylene group represented by $R^3$ is preferably a linear or branched alkylene group having 1 to 30 carbon atoms, more preferably a linear or branched alkylene group having 2 to 20 carbon atoms, and most preferably a linear or branched alkylene group having 2 to 5 carbon atoms. Examples of the substituent, which the alkylene group may have, include those listed as examples of the substituent of the above alkyl group.

As the cyclic alkylene group represented by $R^3$, those having 3 to 30 carbon atoms except for carbon atoms of the substituent are preferred. Examples of the cycloalkylene group include a cyclopentylene group, a cyclohexylene group, a cycloheptylene group, and a cyclooctylene group. Examples of the substituent, which the cycloalkylene group may have, include those listed as examples of the substituent of the above alkyl group.

$R^3$ is preferably a substituted or unsubstituted alkylene group in particular.

$X^1$ in Formula (I) represents a halogen atom. From the viewpoints of ease in handling and cost for an acid halogenating agent to be used, a chlorine atom or a bromine atom is preferred, and a chlorine atom is most preferred.

$L^1$ represents a leaving group. Examples of the leaving group include known leaving groups. Among these groups, a halogen atom (fluorine, chlorine, bromine, iodine), and a sulfonyloxy group (for example, a mesyl group, a tosyl group, a trifluoromethanesulfonyloxy group) are preferred. A chlorine atom or a bromine atom is more preferred. A chlorine atom is most preferred.

In Formula (I), the following combination is preferred: $R^1$ is an alkyl group having 2 to 10 carbon atoms; $R^2$ is an alkyl group having 2 to 10 carbon atoms; $R^3$ is an alkylene group having 2 to 10 carbon atoms; $X^1$ is a chlorine atom or a bromine atom; and $L^1$ is a chlorine atom or a bromine atom. Further, the following combination is more preferred: $R^1$ is an alkyl group having 2 to 5 carbon atoms; $R^2$ is an alkyl group having 2 to 5 carbon atoms; $R^3$ is an alkylene group having 2 to 5 carbon atoms; $X^1$ is a chlorine atom; and $L^1$ is a chlorine atom.

Specific examples of the compound represented by Formula (I) are shown below. However, the present invention is not limited to these compounds.

Note that in Table showing exemplified compounds, "Me" represents a methyl group; "Et" represents an ethyl group; "Pr" represents a propyl group; "Bu" represents a butyl group; and "Ph" represents a phenyl group.

| Compound | X | $R_A$ | $R_B$ | $R_C$ | $L_A$ |
|---|---|---|---|---|---|
| (I-1) | Cl | Et | Et | —CH$_2$CH$_2$CH$_2$— | Cl |
| (I-2) | Cl | Et | Et | —CH$_2$CH$_2$CH$_2$— | Br |
| (I-3) | Cl | Et | Et | —CH$_2$CH$_2$CH$_2$— | I |
| (I-4) | Cl | Et | Et | —CH$_2$CH$_2$CH$_2$— | MeSO$_3$ |
| (I-5) | Cl | Et | Et | —CH$_2$CH$_2$CH$_2$— | CF$_3$SO$_3$ |
| (I-6) | Cl | Et | Et | —CH$_2$CH$_2$CH$_2$— | TsO |
| (I-7) | Cl | n-Pr | n-Pr | —CH$_2$CH$_2$CH$_2$— | Cl |
| (I-8) | Cl | i-Pr | i-Pr | —CH$_2$CH$_2$CH$_2$— | Cl |
| (I-9) | Cl | Bu | Bu | —CH$_2$CH$_2$CH$_2$— | Cl |
| (I-10) | Cl | sec-Bu | sec-Bu | —CH$_2$CH$_2$CH$_2$— | Cl |
| (I-11) | Cl | tert-Bu | tert-Bu | —CH$_2$CH$_2$CH$_2$— | Cl |
| (I-12) | Cl | Ph | Ph | —CH$_2$CH$_2$CH$_2$— | Cl |
| (I-13) | Cl | Me | i-Pr | —CH$_2$CH$_2$CH$_2$— | Cl |
| (I-14) | Cl | Et | i-Pr | —CH$_2$CH$_2$CH$_2$— | Cl |
| (I-15) | Cl | Bu | n-C$_6$H$_{13}$ | —CH$_2$CH$_2$CH$_2$— | Cl |
| (I-16) | Cl | —CH=CH$_2$ | —CH=CH$_2$ | —CH$_2$CH$_2$CH$_2$— | Cl |
| (I-17) | Cl | —C≡CMe | —C≡CMe | —CH$_2$CH$_2$CH$_2$— | Cl |
| (I-18) | Cl | 2-pyridyl | 2-pyridyl | —CH$_2$CH$_2$CH$_2$— | Cl |
| (I-19) | Cl | —CH$_2$CH=CH$_2$ | —CH$_2$CH=CH$_2$ | —CH$_2$CH$_2$CH$_2$— | Cl |
| (I-20) | Cl | H | tert-Bu | —CH$_2$CH$_2$CH$_2$— | Cl |
| (I-21) | F | Et | Et | —CH$_2$CH$_2$CH$_2$— | Cl |
| (I-22) | Br | Et | Et | —CH$_2$CH$_2$CH$_2$— | Cl |
| (I-23) | I | Et | Et | —CH$_2$CH$_2$CH$_2$— | Cl |
| (I-24) | Cl | Et | Et | —CH$_2$CH$_2$— | Cl |
| (I-25) | Cl | Et | Et | —CH$_2$CH$_2$CH$_2$CH$_2$— | Cl |
| (I-26) | Cl | Et | Et | —CHMeCH$_2$CH$_2$— | Cl |
| (I-27) | Cl | Et | Et | (cyclohexylene) | Cl |
| (I-28) | Cl | Et | Et | 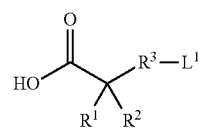 | Cl |
| (I-29) | Cl | Et | Bu | —CH$_2$CH$_2$CH$_2$— | Cl |

<Compound Represented by Formula (II)>

$$\text{(II)}$$

In Formula (II), $R^1$, $R^2$, $R^3$ and $L^1$ have the same definitions as $R^1$, $R^2$, $R^3$ and $L^1$ in the above-described Formula (I), respectively, and $R^1$, $R^2$, $R^3$ and $L^1$ have the same preferable definitions as $R^1$, $R^2$, $R^3$ and $L^1$ in the above-described Formula (I), respectively.

Specific examples of the compound represented by Formula (II) are shown below. However, the present invention is not limited to these compounds.

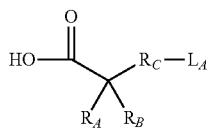

| Compound | $R_A$ | $R_B$ | $R_C$ | $L_A$ |
|---|---|---|---|---|
| (II-1) | Et | Et | —CH$_2$CH$_2$CH$_2$— | Cl |
| (II-2) | Et | Et | —CH$_2$CH$_2$CH$_2$— | Br |
| (II-3) | Et | Et | —CH$_2$CH$_2$CH$_2$— | I |
| (II-4) | Et | Et | —CH$_2$CH$_2$CH$_2$— | MeSO$_3$ |
| (II-5) | Et | Et | —CH$_2$CH$_2$CH$_2$— | CF$_3$SO$_3$ |
| (II-6) | Et | Et | —CH$_2$CH$_2$CH$_2$— | TsO |
| (II-7) | n-Pr | n-Pr | —CH$_2$CH$_2$CH$_2$— | Cl |
| (II-8) | i-Pr | i-Pr | —CH$_2$CH$_2$CH$_2$— | Cl |
| (II-9) | n-Bu | n-Bu | —CH$_2$CH$_2$CH$_2$— | Cl |
| (II-10) | sec-Bu | sec-Bu | —CH$_2$CH$_2$CH$_2$— | Cl |
| (II-11) | tert-Bu | tert-Bu | —CH$_2$CH$_2$CH$_2$— | Cl |
| (II-12) | Ph | Ph | —CH$_2$CH$_2$CH$_2$— | Cl |
| (II-13) | Me | i-Pr | —CH$_2$CH$_2$CH$_2$— | Cl |
| (II-14) | Et | i-Pr | —CH$_2$CH$_2$CH$_2$— | Cl |
| (II-15) | n-Bu | n-C$_6$H$_{13}$ | —CH$_2$CH$_2$CH$_2$— | Cl |
| (II-16) | —CH=CH$_2$ | —CH=CH$_2$ | —CH$_2$CH$_2$CH$_2$— | Cl |
| (II-17) | —C≡CMe | —C≡CMe | —CH$_2$CH$_2$CH$_2$— | Cl |
| (II-18) | 2-pyridyl | 2-pyridyl | —CH$_2$CH$_2$CH$_2$— | Cl |
| (II-19) | —CH$_2$CH=CH$_2$ | —CH$_2$CH=CH$_2$ | —CH$_2$CH$_2$CH$_2$— | Cl |
| (II-20) | H | tert-Bu | —CH$_2$CH$_2$CH$_2$— | Cl |
| (II-21) | Et | Et | —CH$_2$CH$_2$— | Cl |
| (II-22) | Et | Et | —CH$_2$CH$_2$CH$_2$CH$_2$— | Cl |
| (II-23) | Et | Et | —CHMeCH$_2$CH$_2$— | Cl |
| (II-24) | Et | Et | (1,4-cyclohexylene) | Cl |
| (II-25) | Et | Et | —CH(H)—C$_6$H$_4$—CH(H)— | Cl |
| (II-26) | Et | Bu | —CH$_2$CH$_2$CH$_2$— | Cl |

<Compound Represented by Formula (III)>

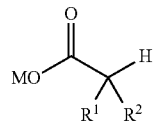

(III)

In Formula (III), $R^1$ and $R^2$ have the same definitions as $R^1$ and $R^2$ in the above-described Formula (I), respectively. M represents a hydrogen atom or a metal atom.

M is preferably a hydrogen atom, an alkali metal atom (for example, lithium, sodium, potassium), an alkaline-earth metal atom (calcium, magnesium), and especially a hydrogen atom and an alkali metal atom are preferred. As the alkali metal atom, a lithium atom, a sodium atom, and a potassium atom are preferred.

<Compound Represented by Formula (IV)>

$$L^2\text{-}R^3\text{-}L^1 \quad (IV)$$

In Formula (IV), $R^3$ and $L^1$ have the same definitions as $R^3$ and $L^1$ in the above-described Formula (I), respectively. $L^2$ represents a leaving group.

The leaving group represented by $L^2$ has the same definition as the leaving group represented by $L^1$ in the above-described Formula (I). However, it is preferred that the leaving group represented by $L^2$ is equal to or higher than the leaving group represented by $L^1$ in terms of elimination properties.

Specifically, in a case in which $L^1$ is a chlorine atom, $L^2$ is preferably a chlorine atom, a bromine atom, an iodine atom, or a sulfonyloxy group, more preferably a bromine atom, or an iodine atom, and most preferably a bromine atom. In a case in which $L^1$ is a bromine atom, $L^2$ is preferably a bromine atom, an iodine atom, or a sulfonyloxy group, more preferably a bromine atom, or an iodine atom, and most preferably an iodine atom. In a case in which $L^1$ is an iodine atom, $L^2$ is preferably an iodine atom. In a case in which $L^1$ is a sulfonate group, $L^2$ is preferably a sulfonate group.

Among combinations of $L^1$ and $L^2$, the combination in which $L^1$ is a chlorine atom, and $L^2$ is a bromine atom is most preferable from the viewpoints of selectivity and cost of raw materials.

Next, the production method of the present invention is described in detail below.

<Process of Reacting Compound Represented by Formula (III) with Basic Compound and Compound Represented by Formula (IV), Thereby Obtaining Compound Represented by Formula (II)>

The process of reacting a compound represented by Formula (III) with a basic compound and a compound represented by Formula (IV) thereby obtaining a compound represented by Formula (II) preferably includes a process of reacting the compound represented by Formula (III) and the basic compound thereby obtaining an intermediate enolate represented by Formula (III-2) (hereinafter, referred to as "enolization process" appropriately) and a process of reacting the enolate and the compound represented by Formula (IV) (hereinafter, referred to as "alkylation process" appropriately).

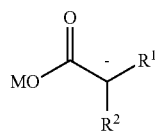
(III-2)

In Formula (III-2), $R^1$, $R^2$ and M have the same definitions as $R^1$, $R^2$ and M in the above-described Formula (III), respectively.

As the basic compound that generates the enolate represented by Formula (III-2), known basic compounds may be used. Examples of the basic compound include an alkyl metal compound (for example, Grignard reagent, methyl lithium, n-butyl lithium, s-butyl lithium, t-butyl lithium, phenyl lithium, triphenylmethyl lithium, triphenylmethyl potassium), a metal amide (for example, sodium amide, potassium amide, lithium diisopropylamide, lithium-2,2,6,6-tetramethylpiperidide, lithium hexamethyldisiladide, sodium hexamethyldisiladide, potassium hexamethyldisiladide), a metal hydride (for example, lithium hydride, sodium hydride, potassium hydride, calcium hydride), a metal hydroxide (for example, lithium hydroxide, sodium hydroxide, potassium hydroxide, calcium hydroxide), and a metal alkoxide (for example, sodium methoxide, sodium ethoxide, sodium tert-butoxide, lithium tert-butoxide, potassium tert-butoxide).

These basic compounds may be used singly or in combination of two or more kinds thereof.

In a case in which M is a hydrogen atom, the basic compound is preferably an alkyl metal compound, a mixture of an alkyl metal compound and a metal amide, a mixture of an alkyl metal compound and a metal hydride, a mixture of an alkyl metal compound and a metal hydroxide, a mixture of an alkyl metal compound and a metal alkoxide, a metal amide, a mixture of a metal amide and a metal hydride, a mixture of a metal amide and a metal hydroxide, and a mixture of a metal amide and a metal alkoxide. Especially, the basic compound is preferably an alkyl metal compound, a mixture of an alkyl metal compound and a metal amide, a mixture of an alkyl metal compound and a metal hydride, a metal amide, and a mixture of a metal amide and a metal hydride.

In a case in which M is a metal atom, the basic compound is preferably an alkyl metal compound, a metal amide, and a metal hydride. Especially an alkyl metal compound or a metal amide is preferred.

In a case in which M in the compound represented by Formula (III) is a hydrogen atom, a use amount of the basic compound is preferably from 2 to 5 moles, more preferably from 2 to 4 moles, and most preferably from 2.0 to 3.5 moles, with respect to one mole of the compound represented by Formula (III). In a case in which M in the compound represented by Formula (III) is a hydrogen atom, a reaction temperature in the enolization process is preferably from −30 to 70° C., more preferably from −20 to 70° C., and most preferably from −10 to 60° C. By controlling the temperature to the above range, the enolate represented by Formula (III-2) becomes easy to be formed, which results in improvement of yield. A reaction time is preferably from 0.5 to 6 hours, more preferably from 0.5 to 4 hours, and most preferably from 0.5 to 3 hours.

In a case in which M in the compound represented by Formula (III) is a metal atom, a use amount of the basic compound is preferably from 1 to 3 moles, more preferably from 1 to 2 moles, and most preferably from 1.1 to 1.5 moles, with respect to one mole of the compound represented by Formula (III). In a case in which M in the compound represented by Formula (III) is a metal atom, a reaction temperature in the enolization process is preferably from −30 to 70° C., more preferably from −20 to 70° C., and most preferably from −10 to 60° C. By controlling the temperature to the above range, the enolate represented by Formula (III-2) becomes easy to be formed, which results in improvement of yield. A reaction time is preferably from 0.5 to 6 hours, more preferably from 0.5 to 4 hours, and most preferably from 0.5 to 3 hours.

A use amount of the compound represented by Formula (III) is preferably from 1 to 10 moles, more preferably from 1 to 5 moles, and most preferably from 1 to 2 moles, with respect to one mole of the compound represented by Formula (IV). A reaction temperature in the alkylation process is preferably from −70 to 20° C., more preferably from −50 to 20° C., and most preferably from −40 to 10° C. from the viewpoint of productivity. By controlling the temperature to the above range, both reaction speed and reaction selectivity are improved, and both yield and purity of the target are increased, which results in improvement of production. A reaction time is preferably from 0.1 to 5 hours, more preferably from 0.5 to 3 hours, and most preferably from 0.5 to 2 hours. The end of reaction can be determined by NMR, a gas chromatography, a high-performance liquid chromatography, or the like.

It is preferred to use an organic solvent in the enolization process and the alkylation process according to the present invention. Although the organic solvent is not particularly limited, examples of the organic solvent include aliphatic hydrocarbon solvents (for example, hexane, heptane), aromatic solvents (for example, benzene, toluene, xylene, mesitylene, chlorobenzene), ether solvents (for example, tetrahydrofuran, diethyl ether, dibutyl ether, diphenyl ether, dimethoxyethane, diglyme), amide solvents (for example, N,N-dimethylformamide, N,N-dimethylacetamide, N-methyl-2-pyrrolidone, N-ethyl-2-pyrrolidone), sulfur-containing solvents (for example, dimethylsulfoxide, sulfolane), hexamethylphosphoric triamide, dimethylethylene urea, dimethylpropylene urea, and tetramethyl urea. Further, these solvents may be used alone or in a mixture of two or more kinds thereof. Ether solvents alone, a mixture of ether solvents and hexamethylphosphoric triamide, and a mixture of ether solvents and dimethylpropylene urea are preferred.

In order to accelerate a progress of the reaction, additives such as crown ethers may be used in the enolization process and the alkylation process according to the present invention.

<Process of Reacting Compound Represented by Formula (II) with Acid Halogenating Agent, Thereby Obtaining Compound Represented by Formula (I)>

The acid halogenating agent that is used in the process of reacting a compound represented by Formula (II) with an acid halogenating agent, thereby obtaining a compound represented by Formula (I) (hereinafter, referred to as "acid halogenating process" appropriately) represents known compounds capable of converting a carboxylic acid to an acid halide. Examples of the acid halogenating agent includes compounds described in the forth edition "Jikken Kagaku Koza 22 Yuki Gosei (Organic Synthesis) IV Acid•Amino Acid•Peptide" pp. 115-127. Among these compounds, thionyl chloride, oxalyl chloride, and phosphorylchloride are preferred, and thionyl chloride is most preferred.

A use amount of the acid halogenating agent is preferably from 1 to 5 mole, and more preferably from 1 to 2 mole, with respect to one mole of the compound represented by Formula (II).

A reaction temperature is preferably from 0 to 100° C., more preferably from 10 to 70° C., and most preferably from 20 to 50° C. A reaction time is preferably from 0.5 to 10 hours.

Favorable yield and purity are achieved by selecting the reaction temperature and the reaction time in the above-described ranges, respectively.

Further, additives may be added to activate the acid halogenating agent. As for the additives, N,N-dimethylformamide and pyridine are preferred. As for the addition amount, the additives are added in an amount of preferably from 0.001 to 1 mole, and most preferably from 0.01 to 0.5 moles, with respect to one mole of the compound represented by Formula (II).

The acid halogenating process according to the present invention is preferably performed in the absence of solvent from the viewpoint of productivity. However, the process may be performed in the presence of solvent. Although the solvent used in the process is not particularly limited, examples of the solvent include aliphatic hydrocarbon solvents (for example, hexane, heptane), aromatic solvents (for example, benzene, toluene, xylene, mesitylene, chlorobenzene), ester solvents (for example, ethyl acetate, butyl acetate), ether solvents (for example, tetrahydrofuran, diethyl ether, dibutyl ether, diphenyl ether), amide solvents (for example, N,N-dimethylformamide, N,N-dimethylacetamide, N-methyl-2-pyrrolidone, N-ethyl-2-pyrrolidone), and sulfur-containing solvents (for example, dimethylsulfoxide, sulfolane). Especially, aromatic solvents and ester solvents are preferred.

Further, theses solvents may be used in combination of two or more kinds thereof.

The thus-obtained compound represented by Formula (I) is preferably subjected to purification by distillation, recrystallization, or the like. However, in a case in which a boiling point of the compound is too high to be distilled, or the compound is not solidified, unreacted acid halogenating agent may be removed by concentration so that a residue can be used in the next stage of the process.

According to an aspect of the invention, there are provided the following embodiments <1> to <5>.

<1> A method of producing an acid halide, comprising:

reacting a compound represented by the following Formula (III) with a basic compound and a compound represented by the following Formula (IV) to obtain a compound represented by the following Formula (II); and reacting the compound represented by Formula (II) with an acid halogenating agent to obtain a compound represented by the following Formula (I):

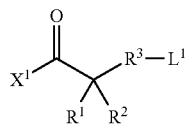
(I)

wherein, in Formula (I), $R^1$ and $R^2$ each independently represent a group selected from the group consisting of an alkyl group, an aryl group, an alkenyl group, an alkynyl group, and a heterocyclic group; $R^3$ represents an alkylene group; $X^1$ represents a halogen atom; and $L^1$ represents a leaving group;

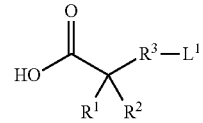
(II)

wherein, in Formula (II), $R^1$, $R^2$, $R^3$ and $L^1$ have the same definitions as $R^1$, $R^2$, $R^3$ and $L^1$ in Formula (I), respectively;

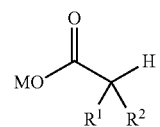
(III)

wherein, in Formula (III), $R^1$ and $R^2$ have the same definitions as $R^1$ and $R^2$ in Formula (I), respectively, and M represents a hydrogen atom or a metal atom;

(IV)

wherein, in Formula (IV), $R^3$ and $L^1$ have the same definitions as $R^3$ and $L^1$ in Formula (I), respectively, and $L^2$ represents a leaving group.

<2> The method of producing an acid halide according to <1>, wherein the reacting of the compound represented by Formula (III) with the basic compound and the compound represented by Formula (IV) to obtain the compound represented by Formula (II) comprises:

reacting the compound represented by Formula (III) with the basic compound to obtain an intermediate enolate represented by the following Formula (III-2); and reacting the obtained enolate represented by Formula (III-2) with the compound represented by Formula (IV):

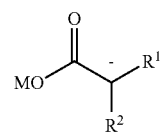
(III-2)

wherein, in Formula (III-2), $R^1$, $R^2$ and M have the same definitions as $R^1$, $R^2$ and M in Formula (III), respectively.

<3> The method of producing an acid halide according to <2>, wherein a temperature at which the compound represented by Formula (III) is reacted with the basic compound to obtain the intermediate enolate represented by Formula (III-2) is in a range of from −30° C. to 70° C.

<4> The method of producing an acid halide according to <2> or <3>, wherein a temperature at which the enolate represented by Formula (III-2) is reacted with the compound represented by Formula (IV) is in a range of from −70° C. to 20° C.

<5> A compound represented by the following Formula (I) and obtained by the production method of <1>:

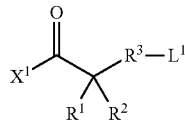

wherein, in Formula (I), $R^1$ and $R^2$ each independently represent a group selected from the group consisting of an alkyl group, an aryl group, an alkenyl group, an alkynyl group, and a heterocyclic group; $R^3$ represents an alkylene group; $X^1$ represents a halogen atom; and $L^1$ represents a leaving group.

The production method of the preset invention makes it possible to provide a method of producing an acid halide having both a leaving group and a bulky group in a short process at low cost and high selectivity. Further, the acid halide having both a leaving group and a bulky group, which is produced by the production method of the preset invention, can be provided.

A high-purity acid halide can be produced by the production method of acid halide according to the preset invention. The acid halide produced by the production method of the preset invention is especially useful for a synthetic intermediate of the functional material that is required a high purity, such as a dye for color filter, a dye for printing, a dye for inkjet, medicines and agricultural chemicals.

EXAMPLES

Hereinafter, the present invention is described more specifically in reference to Examples. However, the present invention is not limited to the following Examples, unless it is beyond the scope of the gist of the present invention.

Example 1

Under a nitrogen atmosphere, 196 g (1.935 mol) of diisopropylamine and 800 ml of tetrahydrofuran (hereinafter, referred to as "THF") were placed in a reactor, and then cooled down to −10° C. To the mixture, 727 ml (1.89 mol) of n-BuLi (2.6 M/hexane solution) as a basic compound was added dropwise over 1 hour. Then, the mixture was stirred at −10° C. for 15 minutes to prepare lithium diisopropylamide in a reaction system. Then, 100 g (0.86 mol) of Compound (A1) having the following structure was added dropwise thereto over 1 hour, and then temperature was elevated up to 40° C. thereby performing an enolization process. After stirring for 2 hours, internal temperature was cooled back down to −10° C., and then 176 g (1.12 mol) of 1-chloro-3-bromopropane was added dropwise thereto over 1 hour, and then stirred at 0° C. for 3 hours thereby performing an alkylation process. After the end of reaction, 1 liter of 6 N-hydrochloric acid and 1 liter of ethyl acetate were added to perform extraction fractionation. The organic layer was washed with water and concentrated, thereby obtaining 205 g of unpurified product of Compound (II-1) having the following structure. Next, in a reactor equipped with a reflux condenser and a basic trap, 205 g of the unpurified product of Compound (II-1) was placed. After filling the inside of the reactor with nitrogen to provide a nitrogen atmosphere, 153 g (1.29 mol) of thionyl chloride was added dropwise over 30 minutes. Thereafter, the reactor was heated until an internal temperature became 30° C., and then stirring was continued for 2 hours. After the end of reaction, thionyl chloride was distilled off under reduced pressure. By distillation under reduced pressure, 146 g (0.70 mole, two-step yield: 80%) of Compound (I-1) having the following structure was obtained.

The reaction scheme and compounds are shown below.

Note that the thus-obtained Compound was identified as the structure of (1-1) by $^1$H-NMR (trade name, GEMINI-300, manufacture by Varian Medical Systems, Inc.).

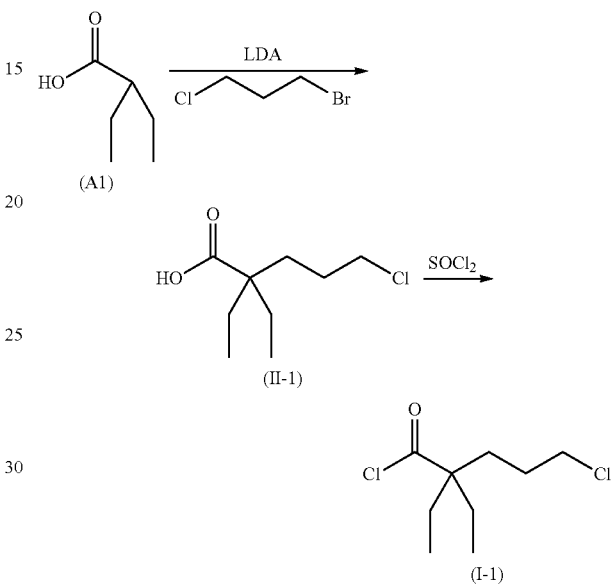

The compound data of Exemplified compound (II-1) is shown below.

$^1$H-NMR (300 MHz, CDCl$_3$): δ0.84 (6H, t), 1.58-1.71 (8H, m), 3.51-3.56 (2H, m)

The compound data of Exemplified compound (I-1) is shown below.

$^1$H-NMR (300 MHz, CDCl$_3$): δ0.87 (6H, t), 1.65-1.84 (8H, m), 3.55 (2H, t)

Example 2

Under a nitrogen atmosphere, 98 g (0.97 mol) of diisopropylamine, 35 g (0.87 mol) of sodium hydride and 800 ml of THF were placed in a reactor, and then cooled down to −10° C. Thereafter, 100 g (0.86 mol) of (A1) were added dropwise thereto over 1 hour and then temperature was elevated up to 40° C. After stirring for 2 hours, temperature was lowered back to 0° C. To the reaction solution, 363 ml (0.95 mol) of n-BuLi (2.6 M/hexane solution) was added dropwise over 1 hour, thereby preparing Lithium diisopropylamide in a reaction system. Next, a temperature of the reaction liquid was elevated up to 40° C. to perform an enolization process. After stirring for 2 hours, the internal temperature was lowered back to −10° C. for cooling, and then 176 g (1.12 mol) of 1-chloro-3-bromopropane was added dropwise over 1 hour, and stirring was continued at 0° C. for 3 hours, thereby performing an alkylation process. After the end of reaction, 1 liter of 6 N-hydrochloric acid and 1 liter of ethyl acetate were added to perform extraction fractionation. The organic layer was washed with water and concentrated, thereby obtaining 218 g of unpurified product of Compound (II-1). Next, in a reactor equipped with a reflux condenser and a basic trap, 218 g of the unpurified product of Compound (II-1) was placed. After filling the inside of the reactor with nitrogen to provide a nitrogen atmosphere, 153 g (1.29 mol) of thionyl chloride was added dropwise over 30 minutes. Thereafter, the reactor was heated until the internal temperature became 30° C., and stirring was continued for 2 hours. After the end of reaction, thionyl chloride was distilled off under reduced pressure. By distillation under reduced pressure, 137 g (0.65 mol, two-step yield: 76%) of Compound (I-1) was obtained.

a use amount (mole) of the basic compound and a use amount (mole) of the acid halogenating agent were the same as those in Example 1 respectively. Thus, Compound (I-1) was obtained In Table 1, each kind of raw materials, basic compounds, and acid halogenating agents, and each temperature of the enolization process and the alkylation process used in Examples 1 to 9, and the raw material used in Comparative Examples 1 and 2 were shown together. Further, each yield (expressed by molar conversion % on the basis of raw material) of the acid halide obtained in each of Examples 1 to 9 and Comparative Examples 1 and 2, and each purity (%) of the obtained acid halide were shown together in Table 1.

Note that LDA in Table 1 represents lithium diisopropylamide.

TABLE 1

| | Raw material | Basic compound | Temperature for enolization (° C.) | Temperature for alkylation (° C.) | Acid halogenating agent | Number of processes | Yield (molar conversion) | Purity |
| --- | --- | --- | --- | --- | --- | --- | --- | --- |
| Example 1 | (A1) | LDA | −10-40 | −10-0 | Thionyl chloride | 2 | 80% | 98% |
| Example 2 | (A1) | NAH + LDA | −10-40 | −10-0 | Thionyl chloride | 2 | 76% | 96% |
| Example 3 | (A1) | LDA | −30--20 | −10-0 | Thionyl chloride | 2 | 68% | 97% |
| Example 4 | (A1) | LDA | −10-40 | 20-30 | Thionyl chloride | 2 | 72% | 94% |
| Example 5 | (A1) | LDA | −10-40 | −10-0 | Oxalyl chloride | 2 | 78% | 97% |
| Example 6 | (A1) | LDA | −10-40 | −10-0 | Phosphoryl chloride | 2 | 77% | 95% |
| Example 7 | (A2) | LDA | −10-40 | −10-0 | Thionyl chloride | 2 | 79% | 98% |
| Example 8 | (A3) | LDA | −10-40 | −10-0 | Thionyl chloride | 2 | 75% | 97% |
| Example 9 | (A4) | LDA | −10-40 | −10-0 | Thionyl chloride | 2 | 76% | 98% |
| Comparative Example 1 | (A7) | — | — | — | Thionyl chloride | 3 | 66% | 72% |
| Comparative Example 2 | (A7) | — | — | — | Thionyl chloride | 3 | 52% | 92% |

The reaction scheme and compounds are shown below.

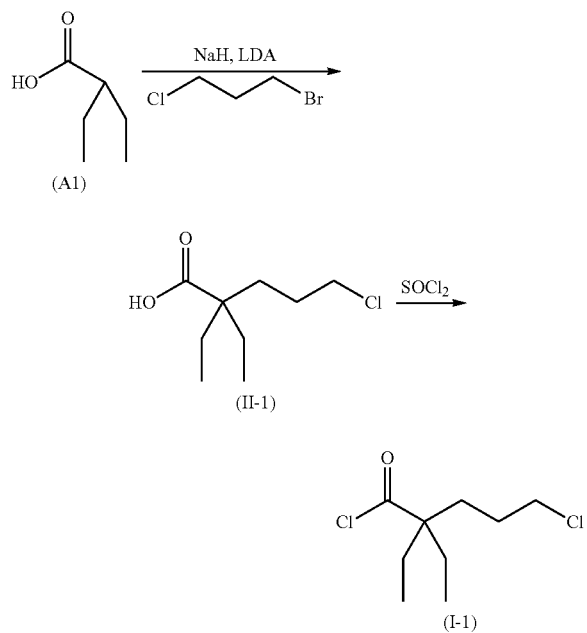

Examples 3 to 6

Examples 3 to 6 were conducted in the same manner as in Example 1, except that each reaction temperature in Example 1 was changed to those shown in the following Table 1, and the kind of basic compound and the kind of acid halogenating agent in Example 1 were changed as shown in Table 1, while Example 7

Under a nitrogen atmosphere, 98 g (0.97 mol) of diisopropylamine and 800 ml of THF were placed in a reactor, and then cooled down to 0° C. To the reaction solution, 363 ml (0.95 mol) of n-BuLi (2.6 M/hexane solution) was added dropwise over 1 hour. Next, after stirring at −10° C. for 15 minutes, 119 g (0.86 mol) of Compound (A2) having the following structure was added dropwise thereto over 1 hour, and then temperature was elevated up to 40° C. thereby performing an enolization process. After stirring for 2 hours, the internal temperature was lowered back to −10° C., and then 176 g (1.12 mol) of 1-chloro-3-bromopropane was added dropwise thereto over 1 hour, and then stirred at 0° C. for 3 hours thereby performing an alkylation process. After the end of reaction, 1 liter of 6 N-hydrochloric acid and 1 liter of ethyl acetate were added to perform extraction fractionation. The organic layer was washed with water and concentrated, thereby obtaining 198 g of unpurified product of Compound (II-1). Next, in a reactor equipped with a reflux condenser and a basic trap, 198 g of the unpurified product of Compound (II-1) was placed. After filling the inside of the reactor with nitrogen to provide a nitrogen atmosphere, 153 g (1.29 mol) of thionyl chloride was added dropwise over 30 minutes. Thereafter, the reactor was heated until an internal temperature became 30° C., and stirring was continued for 2 hours. After the end of reaction, thionyl chloride was distilled off under reduced pressure. By distillation under reduced pressure, 144 g (0.68 mole, two-step yield: 79%) of Compound (I-1) was obtained.

The reaction scheme and compounds are shown below.

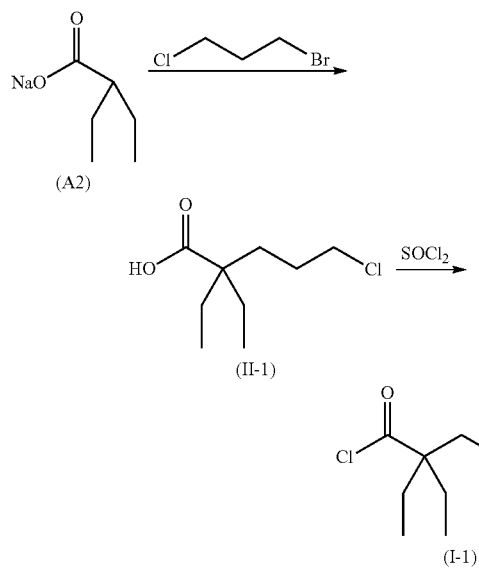

Examples 8 and 9

Examples 8 and 9 were conducted in the same manner as in Example 1, except that Compound (A1) used in Example 1 was changed to Compound (A3) and Compound (A4) having the following structures, respectively. The thus-obtained acid halides were identified respectively as Exemplified compound (I-29) and Exemplified compound (I-7).

Note that each of compounds (A3) and (A4) was used in the same molar amount as that of Compound (A 1) in Example 1.

Note that the thus-obtained compounds were identified respectively as Exemplified compounds (I-29) and (I-7) by $^1$H-NMR (GEMINI-300, trade name, manufacture by Varian Medical Systems, Inc.).

Exemplified compound (I-29): $^1$H-NMR (300 MHz, CDCl$_3$): δ0.82 (3H, t), 0.87 t), 1.65-1.84 (12H, m), 3.54 (2H, t)

Exemplified compound (I-7): $^1$H-NMR (300 MHz, CDCl$_3$): δ0.86 (6H, t), 1.63-1.85 (12H, m), 3.53 (2H, t)

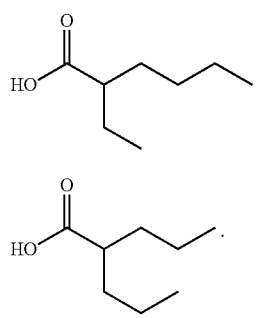

Comparative Example 1

Under a nitrogen atmosphere, 100 g (1.0 mol) of diisopropylamine and 500 ml of tetrahydrofuran were placed in a reactor, and then cooled down to −10° C. Next, to the mixture, 353 ml (0.92 mol) of a n-BuLi/hexane solution having the concentration of 2.6 mol per liter was added dropwise over 1 hour to prepare lithium diisopropylamide in a reaction system. Next, 123 g (0.85 mol) of Compound (A7) was added dropwise thereto over 1 hour at a range of from −10 to 10° C. (a temperature for the enolization process). After stirring for 1 hour, 198.0 g (1.3 mol) of 3-chloro-1-bromopropane was added dropwise thereto over 2 hour. In this time, a reaction temperature was controlled in a range of from −10 to 10° C. (temperature for the alkylation process). After stirring at 0° C. for 1 hour, 300 ml of water was added to perform extraction fractionation. The resultant oil layer was washed twice with an aqueous solution composed of 100 ml of concentrated hydrochloric acid and 200 ml of water, and then once with a saturated sodium bicarbonate aqueous solution. The thus-obtained oil layer was dried with magnesium sulfate and then concentrated, thereby obtaining Compound (III-A) having the following structure. 112 g (1.0 mol) of a 50% by mass potassium hydroxide aqueous solution and 500 g of ethanol were added thereto and heated at the external temperature of 80° C. for 4 hours. After concentration of the solvent, extraction fractionation was conducted with 500 ml of ethyl acetate and 500 ml of a 1 N-hydrochloric acid. The resultant oil layer was concentrated, and then 154.7 g (1.3 mol) of thionyl chloride was added thereto and heated at 50° C. for 2 hours. This reaction mixture was subjected to distillation under reduced pressure (boiling point: 90° C./1 mm Hg), thereby obtaining 118.4 g (0.56 mol) of Compound (I-1) having the following structure. The yield was 66% based on Compound (A7). The purity in accordance with gas chromatography measurement was 72%, while 20% of a total amount of the product was Compound (I-1)' having the following structure formed due to dehydrochlorination.

The reaction scheme and compounds are shown below.

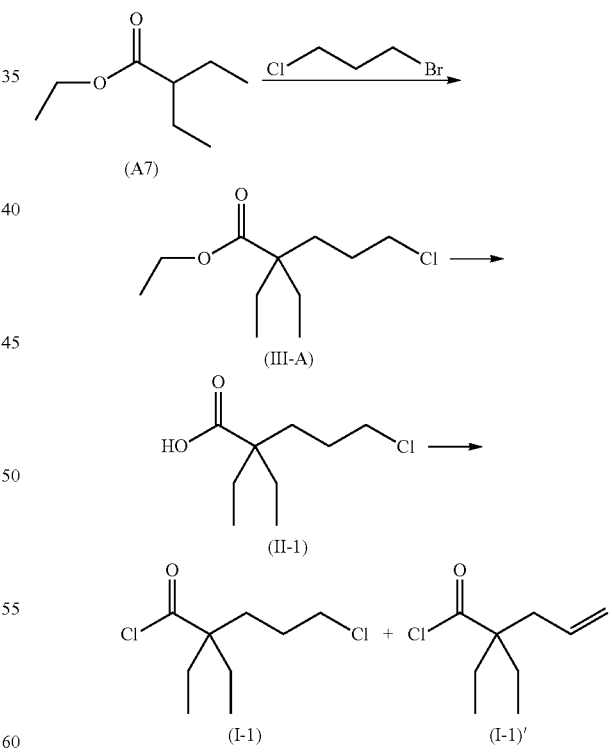

Comparative Example 2

Compound (III-A) having the following structure was obtained in the same operation as in Comparative Example 1. To this product, 20 g (0.1 mol) of trimethylsilyl iodide, 50 g of water and 500 g of ethanol were added and heated at the external temperature of 80° C. It took 144 hours to end the reaction. After concentration of the solvent, extraction fractionation was conducted with 500 ml of ethyl acetate and 500 ml of a 1 N-hydrochloric acid. The resultant oil layer was concentrated, and then 154.7 g (1.3 mol) of thionyl chloride was added thereto and heated at 50° C. for 2 hours. This reaction mixture was subjected to distillation under reduced pressure (boiling point: 90° C./1 mm Hg), thereby obtaining 92.9 g (0.44 mol) of Compound (I-1) having the following structure. The yield was 52% based on Compound (A7). The purity in accordance with gas chromatography measurement was 92%.

The reaction scheme and compounds are shown below.

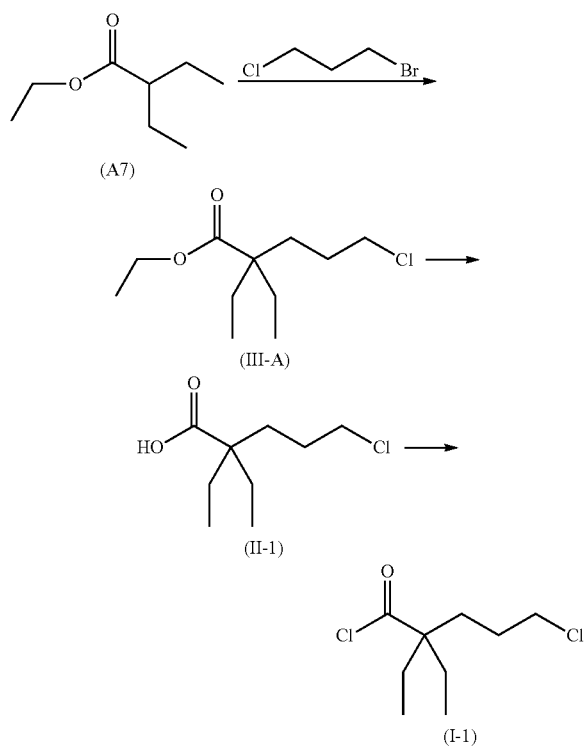

All publications, patent applications, and technical standards mentioned in this specification are herein incorporated by reference to the same extent as if each individual publication, patent application, or technical standard was specifically and individually indicated to be incorporated by reference.

What is claimed is:

1. A compound represented by the following Formula (I-1), (I-7) or (I-29):

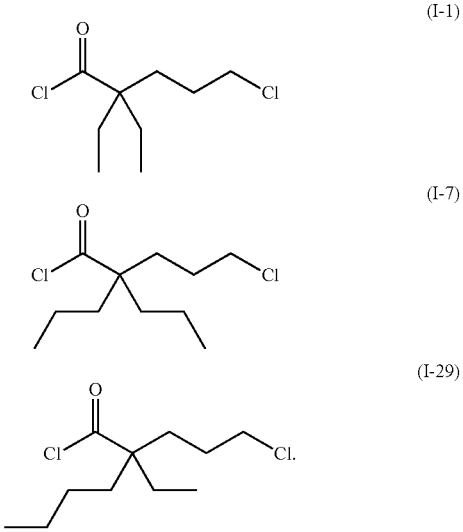

2. The compound according to claim 1, represented by the following formula (I-1):

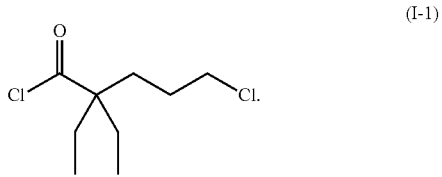

* * * * *